United States Patent [19]

Denzinger et al.

[11] 4,402,937

[45] Sep. 6, 1983

[54] PREPARATION OF PVP-IODINE

[75] Inventors: Walter Denzinger, Speyer; Heinrich Hartmann, Limburgerhof; Wolfgang Schwarz, Ludwigshafen, all of Fed. Rep. of Germany

[73] Assignee: BASF Aktiengesellschaft, Fed. Rep. of Germany

[21] Appl. No.: 188,908

[22] Filed: Sep. 19, 1980

[30] Foreign Application Priority Data

Oct. 18, 1979 [DE] Fed. Rep. of Germany ....... 2942179

[51] Int. Cl.³ .................... A61K 31/79; A61K 33/18
[52] U.S. Cl. ........................................ 424/80; 424/150
[58] Field of Search .................................. 424/150, 80

[56] References Cited

U.S. PATENT DOCUMENTS

| 2,706,701 | 4/1955 | Beller et al. | 424/80 |
| 2,739,922 | 3/1956 | Shelanski | 424/80 |
| 2,826,532 | 3/1958 | Hosmer | 424/80 |
| 2,900,305 | 8/1959 | Siggia | 424/80 |
| 2,914,516 | 11/1959 | Siggia et al. | 260/88.3 |
| 3,028,300 | 4/1962 | Cantor et al. | 424/150 |
| 3,898,326 | 8/1975 | Cantor et al. | 424/80 |
| 4,027,083 | 5/1977 | Herrle et al. | 526/23 |
| 4,058,655 | 11/1977 | Denzinger et al. | 526/212 |
| 4,094,967 | 6/1978 | Gilbert | 424/28 |
| 4,128,633 | 12/1978 | Lorenz | 424/80 |
| 4,200,710 | 4/1980 | Denzinger et al. | 525/326 |
| 4,271,149 | 6/1981 | Wincov et al. | 424/150 |

Primary Examiner—Leonard Schenkman
Attorney, Agent, or Firm—Keil & Witherspoon

[57] ABSTRACT

A process for the preparation of PVP-iodine having an iodine:iodide ratio of about 2:1 and a partition coefficient of 180–250, by reacting PVP with elementary iodine in the presence of formic acid, oxalic acid or an ammonium salt or amide of carbonic acid, formic acid or oxalic acid, in aqueous solution.

3 Claims, No Drawings

PREPARATION OF PVP-IODINE

The present invention relates to a process for the preparation of PVP-iodine. PVP-iodine is the reaction product of polyvinylpyrrolidone (PVP) with elementary iodine, and is finding increasing use because of its germicidal, bactericidal, fungicidal and disinfectant properties.

PVP-iodine is in general marketed as a brown powder which contains about 11% of available iodine, ie. active iodine which can be titrated with sodium thiosulfate, and in addition contains about 5.5% of iodine in the form of iodide. At an iodine:iodide ratio of 2:1, the iodine bonding in the PVP-iodine complex is so strong that an iodine odor is no longer perceptible and a moist potassium iodide/starch paper introduced into the gas space above the PVP-iodine no longer acquires a color. In practice, the measure employed to assess whether the iodine is sufficiently firmly bonded is the partition coefficient of the iodine between an aqueous PVP-iodine solution and heptane and this coefficient, as described, for example, in U.S. Pat. No. 3,028,300, is about should be about 200. Further it is necessary that in its formulations, in particular in aqueous solution, the PVP-iodine should lose very little available iodine on storage, ie. should be very stable.

Very diverse measures have been described for the preparation of a very stable PVP-iodine. For example, according to German Pat. No. 1,037,075, the pulverulent PVP-iodine is subjected to a lengthy heat aftertreatment at 90°-100° C., whilst U.S. Pat. No. 2,900,305 proposes using a PVP having a defined moisture content for the preparation of a suitable PVP-iodine. U.S. Pat. No. 2,826,532 discloses the addition of sodium bicarbonate, and U.S. Pat. No. 3,028,300 the addition of iodide in the form of hydrogen iodide or of an alkali metal iodide. U.S. Pat. No. 3,898,326 proposes the addition of hydrogen iodide or of an alkali metal iodide to an aqueous PVP solution, followed by reaction of the pulverulent PVP-iodide mixture, obtained from the solution after drying, with iodine. German Published Application DAS No. 2,439,197 states that polyvinylpyrrolidone polymerized in an anhydrous organic solvent is particularly suitable for the preparation of a stable PVP-iodine.

The above prior art processes are also intended to permit economical preparation of a stable PVP-iodine. However, they also suffer from substantial disadvantages. According to the process described in German Pat. No. 1,037,075, heating for from 18 to 64 hours at 90°-100° C. to form the PVP-iodine complex is necessary if a stable product having an iodine:iodide ratio of 2:1 is to be obtained. The process described in U.S. Pat. No. 2,900,305 also as a rule entails heating for 22 hours. Heating by the latter process is made additionally difficult by the fact that due to the required higher water content, namely 4-15%, of the polyvinylpyrrolidone used, the heating must in practice be carried out at below 90° C. to avoid caking of the mixture of polyvinylpyrrolidone and iodine, and consequently the heating time required is even longer than in the case of normal pulverulent polyvinylpyrrolidone which usually has a water content of up to 5% by weight.

According to the process of U.S. Pat. No. 3,028,300, the heating is dispensed with by adding iodide in the form of an alkali metal iodide or of hydriodic acid to the mixture of polyvinylpyrrolidone and iodine. This process, again, does not represent an optimum, since inhomogeneous mixtures are formed, in which the iodine is only weakly bonded and which therefore have a strong smell of iodine. Hence, U.S. Pat. No. 3,898,326 proposes adding iodides to an aqueous polyvinylpyrrolidone solution, which is subsequently dried, after which the pulverulent polyvinylpyrrolidone/iodide mixture is reacted with iodine, without a heat treatment. If, according to the above U.S. Pat. No. 3,898,326, the iodide is added as hydriodic acid to the polyvinylpyrrolidone, substantial corrosion problems arise on drying, whilst if the iodide is added as an alkali metal iodide, the PVP-iodine, because of its alkali metal content, no longer conforms to the stringent requirements of the drug laws.

German Published Application DAS No. 2,439,197 also indicates that the heating time is as a rule 10 hours, but to achieve partition coefficients of about 200 it is necessary to heat for at least 20 hours.

The heating times can be greatly reduced if, in accordance with German Published Application DAS No. 2,818,767, PVP is reacted with elementary iodine in the presence of formic acid or oxalic acid or of an ammonium salt or amide of carbonic acid, formic acid or oxalic acid. It is true that aqueous solutions prepared from the PVP-iodine thus obtained are relatively stable, but they lose iodine in the course of time, which substantially limits their shelf life.

German Pat. No. 902,170 discloses combining a Lugol solution with PVP. Lugol solution is an aqueous solution containing iodine and potassium iodide in the ratio of 1:2. Such solutions have the disadvantage that if a commercial PVP (usually prepared, in accordance with German Pat. No. 922,378, by polymerization of vinylpyrrolidone in aqueous solution in the presence of hydrogen peroxide) is used as the starting material, the content of active iodine rapidly drops on storage of the solutions. According to German Laid-Open Application DOS No. 2,540,170, this disadvantage is avoided by using a PVP which is obtained by polymerization in organic solvents, using organic initiators, with or without a steam treatment after polymerization. The aqueous PVP-iodine solution is then obtained by dissolving a compound which provides iodide ions, preferably sodium iodide or potassium iodide, in the aqueous PVP solution.

It is true that this last-mentioned process gives a PVP solution of stable iodine content if an alkali metal iodide is used as the compound which furnishes iodide ions, but, because of their ash content, such iodophores do not conform to the stipulations of the U.S. Pharmacopeia XIX. They are therefore not allowed for use in pharmaceutical formulations. It is true that if hydriodic acid is used as the iodide ion donor compound, the iodophores conform to the stipulations of the U.S. Pharmacopeia, but they are not stable on storage. Additionally, hydriodic acid is extremely difficult to handle because of its very high corrosiveness.

It is an object of the present invention to provide a process for the preparation of more stable aqueous PVP-iodine solutions.

We have found that this object is achieved by a process for the preparation of PVP-iodine, having an iodine:iodide ratio of about 2:1 and a partition coefficient of 180-250, by reacting PVP with elementary iodine in the presence of formic acid, oxalic acid or an ammonium salt or amide of carbonic acid, formic acid or oxalic acid, wherein the reaction is carried out in aqueous solution.

Examples of compounds which accelerate the iodide formation, in addition to the above acids, are ammonium carbonate, ammonium bicarbonate, ammonium carbamate, urea, ammonium formate, formamide, ammonium oxalate, oxamic acid and oxamide.

Oxalic acid and formic acid, which on reaction with iodine give only carbon dioxide in addition to hydrogen iodide, and the amides and ammonium salts of these acids, are particularly preferred.

The amount of the additive, which accelerates iodide formation, is as a rule chosen so that on complete reaction from one-fifth to one-third of the iodine added to the aqueous polyvinylpyrrolidone solution is converted to iodide. Based on iodine employed, the amount is from 2 to 30% by weight, preferably from 4 to 22% by weight, depending on the nature of the additive.

If the polyvinylpyrrolidone solution is mixed with the iodine in conventional stirred reactors, it is advantageous to admix the iodide-forming additive directly. A preferred embodiment is to mix the iodide-forming additive directly into the polyvinylpyrrolidone solution and only then to add the iodine.

Advantageously, the mixing of the polyvinylpyrrolidone with the additive according to the invention and the iodine is carried out first at room temperature or slightly above, up to about 50° C., until the elementary iodine has dissolved in the polyvinylpyrrolidone solution. The heating, to form the iodide, is then carried out at 50°–80° C., in which case the partition coefficient of about 200, which is characteristic of stable PVP-iodine, and an iodine:iodide ratio of 2:1, are in general reached after from 0.5 to 30 hours, with the resulting PVP-iodine having an available iodine content of from 5 to 20% by weight (based on solids).

The polyvinylpyrrolidone employed usually has a K value of from 8 to 50, the range from 10 to 35 being preferred. The process according to the invention is very particularly suitable for a polyvinylpyrrolidone having a K value of from 10 to 20.

A polyvinylpyrrolidone which is particularly suitable for the process according to the invention is prepared by polymerization in an organic solvent, such as isopropanol or toluene, using an organic per-compound, eg. a dialkyl peroxide, as a source of free radicals, with or without a subsequent steam distillation, as described, for example, in German Laid-Open Application DOS 2,515,127.

Polyvinylpyrrolidones which after polymerization are subjected to a hydrogenation treatment are also exceptionally suitable for the preparation of the stable PVP-iodine solutions. The hydrogenation of the polyvinylpyrrolidone is carried out in accordance with conventional known processes, for example with hydrogen in the presence of a suitable catalyst or by treatment with a complex hydride. Advantageously, the hydrogenation is carried out with hydrogen in aqueous solution at from 20° to 100° C., preferably from 50° to 80° C., under a pressure of from 50 to 500 bar, preferably from 200 to 300 bar, in the course of from 1 to 24 hours, cf. U.S. Pat. No. 2,914,516. Suitable catalysts are the conventional platinum and palladium catalysts, and, in particular, Raney nickel.

A particularly preferred embodiment of the hydrogenation is to treat the polyvinylpyrrolidone with a complex hydride, using from 0.1 to 10%, preferably from 0.5 to 5%, thereof, based on the weight of the polymer.

Hydrides used are in particular those which are water-soluble, eg. sodium boranate and lithium boranate, but the reaction can also be carried out with others, eg. $NaBH(OCH_3)_3$, $NaAlH_4$, $LiAlH_4$, $NaAlH_2(OCH_2OCH_3)_2$ or $LiAlH[OC(CH_3)_3]_3$. The lactam group of the polyvinylpyrrolidone is not attacked by this treatment.

The reaction with the complex hydride is carried out in water, where possible; this is feasible with lithium boranate and sodium boranate. For the other hydrides, it is advantageous to use solvents, such as lower alcohols, eg. methanol, ethanol, isopropanol, n-propanol, n-butanol or tert.-butanol, ethers, eg. dioxane or tetrahydrofuran, or aromatics, eg. benzene, toluene or xylene. The reaction is carried out at from 1° to 150° C., preferably from 15° to 80° C., depending on the boiling point of the solvent. If the reaction is carried out in an aqueous or alcoholic solvent, the pH is in general brought to about 7 before the reaction. The reaction time varies from 0.5 to 24 hours, preferably from 2 to 8 hours. If the polyvinylpyrrolidone contains carboxyl groups, it can be advantageous to esterify these, by conventional methods, prior to the reaction with the hydride.

In order to remove impurities which may be present in the polymer, it has proved very useful to purify the polymer solution, after the reaction with the complex hydride, by treatment with an ion exchanger. Examples of suitable ion exchangers are those based on polystyrene and possessing sulfo, carboxyl or quaternary ammonium groups, or those based on acidic or basic silicates.

In the preparation of the aqueous PVP-iodine solutions, the starting material is advantageously an aqueous PVP solution of from 10 to 60% strength by weight, the higher concentrations applying to polymers of low K value, and vice versa.

The PVP-iodine solutions prepared according to the invention can be directly compounded in a conventional manner, with addition of auxiliaries, eg. surfactants, to form end products intended for the consumer. These solutions in general have a total solids concentration of from 10 to 50% by weight.

Surprisingly, the stability of the novel PVP-iodine solutions is about 50% higher than that of solutions obtained by dissolving a PVP-iodine prepared according to German Published Application DAS No. 2,818,767.

A further great advantage compared to the process of German Published Application DAS No. 2,818,767 is that the PVP can be employed directly as a solution and need not be isolated from the aqueous solution.

If desired, a solid product can however be isolated from the aqueous PVP-iodine solution by a drying process, for example by drum drying, spray drying or spray granulation.

The Examples which follow illustrate the invention. Parts are by weight. The K values are determined in aqueous solution, by the method of H. Fikentscher, Cellulose-Chemie, 13 (1932), 38–64 and 71–74. The iodine loss is determined by storing an aqueous PVP-iodine solution, having an available iodine content of 1%, for 15 hours at 80° C. The relatively high temperature of 80° C. has the advantage that the more troublesome storage for 14 days at 52° C. can be avoided, whilst obtaining comparable values. The partition coefficient (PC) is determined in accordance with U.S. Pat. No. 3,028,300 by vigorously shaking 1.0 ml of an aqueous PVP-iodine solution having an available iodine content of 1.0%, with 25 ml of heptane for one minute in a closed glass flask in a thermostated heating bath at 25.0° C. After the mixture has stood for several minutes, the two phases are separated and the iodine content of the aqueous phase is determined by titration with sodium thiosulfate, and the iodine content of the heptane phase is determined spectrophotometrically. The result is calculated from the following equation:

$$PC = \frac{\text{mg of iodine in the H}_2\text{O phase}}{\text{mg of iodine in heptane}} \times \frac{\text{ml of heptane (25)}}{\text{ml of H}_2\text{O phase (1)}}$$

The polyvinylpyrrolidone solutions used in Examples 3 and 4 were prepared in accordance with the following methods:

A. 300 parts of a mixture of 300 parts of vinylpyrrolidone, 700 parts of isopropanol and 12 parts of ditertiary butyl peroxide are introduced into a stirred pressure autoclave and heated to 145° C., resulting in about 7.5 bar gauge pressure in the apparatus. The remainder of the mixture is then introduced at a uniform rate in the course of 3 hours. Heating is then continued for 1 hour, after which the residual vinylpyrrolidone monomer content is less than 0.5%. The mixture is then cooled to 80° C. by releasing the pressure, about 570 parts of isopropanol being distilled off in the course thereof. The residue is then diluted with 100 parts of water and the remaining isopropanol distilled off by passing steam into the mixture. When the temperature at which the steam passes over has reached 98° C., the solution is flushed out with a further 90 parts of steam. The solids content of the solution is then brought to 50% by adding water. The K value of the PVP is 12.5.

B. 750 parts of vinylpyrrolidone are dissolved in 250 parts of water, 0.5 part of an 0.01% strength copper-II chloride solution and 30 parts of 30% strength hydrogen peroxide are added and the mixture is polymerized for 6 hours at 70° C. at a pH of 7.6. The polymer obtained has a K value of 17. When the solution has cooled, it is diluted to 40% strength, 15 parts of sodium boranate are added and the batch is stirred for 12 hours. It is then purified by successive treatment with 10 liters of a cation exchanger (®Lewatit S 100) and 10 liters of an anionic exchanger (®Lewatit M 500). The solids content of the solution is 40%.

EXAMPLE 1

273 parts of a polyvinylpyrrolidone solution are prepared, in a stirred reactor, in accordance with Example I of German Published Application DAS No. 2,818,767, 1.05 parts of formic acid are added and the mixture is brought to pH 7.0 with aqueous ammonia solution. 18 parts of ground iodine are then introduced and the mixture is stirred for about 2 hours, until there is no further detectable foaming (resulting from the evolution of carbon dioxide), after which it is heated for 20 hours at 70° C.

The homogeneous PVP-iodine solution has the following characteristic data:
Available iodine content: 4.1%
Partition coefficient: 207
Iodine loss: 2.8%

EXAMPLE 2

Following a method similar to Example 1, 0.8 part of formic acid is added to 207 parts of polyvinylpyrrolidone prepared according to Example II of German Published Application DAS No. 2,818,767, the pH is brought to 8.0 with aqueous ammonia solution and 17 parts of iodine are introduced. After mixing for 2 hours at room temperature, the batch is heated for 5 hours at 80° C.

The homogeneous PVP-iodine solution has the following characteristic data:
Available iodine content: 5.1%
Partition coefficient: 202
Iodine loss: 8%

EXAMPLE 3

Following a method similar to Example 1, 0.75 parts of formic acid is added to 166 parts of polyvinylpyrrolidone solution, prepared by method A, and 17 parts of iodine are then introduced. After mixing for 2 hours at room temperature, the batch is heated for 2 hours at 75° C.

The homogeneous PVP-iodine solution has the following characteristic data:
Available iodine content: 6.2%
Partition coefficient: 194
Iodine loss: 14%

EXAMPLE 4

Following a method similar to Example 1, 1.35 parts of anhydrous oxalic acid are added to 207 parts of polyvinylpyrrolidone solution, prepared by method B, the mixture is brought to a pH of 8.5 with aqueous ammonia solution, and 17 parts of iodine are then introduced. After mixing for 2 hours at room temperature, the batch is heated for 30 hours at 65° C.

The homogeneous PVP-iodine solution has the following characteristic data:
Available iodine content: 5.0%
Partition coefficient: 220
Iodine loss: 9%

EXAMPLE 5

Following a method similar to Example 1, the amounts, shown in the Table below, of polyvinylpyrrolidone prepared according to Example II of German Published Application DAS 2,818,767, of the compound which accelerates iodide ion formation, and of iodine are mixed and the mixture is stirred for 2 hours at room temperature and then heated for 5 hours at 80° C. The data are shown in the Table below:

| Batch | Polyvinylpyrrolidone solution [parts] | Compound which accelerates iodide ion formation [parts] | Iodine [parts] | Available iodine content [%] | PC | Iodine loss |
|---|---|---|---|---|---|---|
| a | 200 | 1.0 of formamide | 20 | 6.2 | 220 | 7.6% |
| b | 225 | 1.3 of ammonium carbamate | 10 | 3.0 | 198 | 7.5% |
| c | 190 | 3.5 of ammonium | 24 | 7.8 | 212 | 6.9% |

We claim:

1. A process for the preparation of PVP-iodine having an iodine:iodide ratio of about 2:1, a partition coefficient of 180–250 and an iodine content of from about 5 to 20% by weight based on the weight of the solids which comprises: reacting PVP having a K value of from 10 to 35 with elementary iodine in the presence of formic acid, oxalic acid or an ammonium salt or amide of carbonic acid, formic acid or oxalic acid, said reaction being carried out in aqueous solution.

2. The process of claim 1, wherein formic acid, oxalic acid or an ammonium salt or amide of carbonic acid, formic acid or oxalic acid is added to an aqueous solution of PVP containing from 10 to 60% by weight of PVP and wherein elemental iodine is added to the solution and reacted therein with PVP.

3. The process of claim 2, wherein elemental iodine is added to the PVP solution at a temperature of from about room temperature to about 50° C. and is mixed with the solution until the iodine is dissolved, and wherein the solution is then heated at from about 50° to 80° C. for a sufficient period of time to produce an iodine:iodide ratio of 2:1 and to form a PVP-iodine having an available iodine content of from 5 to 20% by weight based on the weight of the solids.

* * * * *